(12) United States Patent
Bleisch et al.

(10) Patent No.: US 6,486,175 B1
(45) Date of Patent: Nov. 26, 2002

(54) DIESTER PRODRUGS OF A DECAHYDROISOQUINOLINE -3-CARBOXYLIC ACID

(75) Inventors: Thomas John Bleisch, Noblesville, IN (US); Edward Louis Mattiuz, Fishers, IN (US); Paul Leslie Ornstein, Carmel, IN (US); Robert Eugene Stratford, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/018,038

(22) PCT Filed: Jun. 13, 2000

(86) PCT No.: PCT/US00/15030

§ 371 (c)(1),
(2), (4) Date: Dec. 11, 2001

(87) PCT Pub. No.: WO01/02367

PCT Pub. Date: Jan. 11, 2001

Related U.S. Application Data

(60) Provisional application No. 60/142,484, filed on Jul. 6, 1999.

(51) Int. Cl.⁷ .................. C07D 217/06; A61K 31/47
(52) U.S. Cl. .................................. 514/307; 546/147
(58) Field of Search ...................... 546/147; 514/307

(56) References Cited

U.S. PATENT DOCUMENTS 5,446,051 A    8/1995  Ornstein .................. 519/307

FOREIGN PATENT DOCUMENTS

| EP | 0560789 A | 4/1994 |
| WO | WO 98/45270 A | 10/1998 |

OTHER PUBLICATIONS

Buchwald, P. and Bodor, N., Quantitative Structure–Metabolism Relationships: Steric and Nonsteric Effects in the Enzymatic Hydrolysis of noncongener Carboxylic Esters, J. Med. Chem. 42, 5160–5168, 1999.

Tanino, T., Ogiso, t., Iwaki, M., Tanabe, G. and Muraoka, O., Enhancement of Oral Bioavailability of Phenytoin by Esterification, and in vitro Hydrolytic Characteristics of Prodrugs, International Journal of Pharmaceutics 163, 91–102, 1998.

Shindo, H. Fukuda, K., Kawai, K. and Tanaka, K., Studies on Intestinal Absorption of Pivampicillin and Species Difference in the Intestinal Esterase Activity, J. Pharm. Dyn. 1, 310–323, 1978.

*Primary Examiner*—Zinna Northington Davis
(74) *Attorney, Agent, or Firm*—Alexander Wilson

(57) ABSTRACT

The present invention relates to novel prodrug forms of 3S,4aR,6S,8aR-6-(((4-carboxy)phenyl)methyl)-1,2,3,4,4a,5,6,7,8,8a-decahydroisoquinoline-3-carboxylic acid, to pharmaceutical compositions containing the prodrug forms, and to methods of using the prodrug forms.

13 Claims, No Drawings

DIESTER PRODRUGS OF A DECAHYDROISOQUINOLINE -3-CARBOXYLIC ACID

This application is a 371 application of PCT/US00/15030 filed Jun. 13, 2000 which claims the benefit of Priority to provisional application Serial No. 60/142,484 filed Jul. 6, 1999.

The present invention relates to novel prodrug forms of 3S,4aR,6S,8aR-6-(((4-carboxy)phenyl)methyl)-1,2,3,4,4a,5,6,7,8,8a-decahydroisoquinoline-3-carboxylic acid, to pharmaceutical compositions containing the prodrug forms, and to methods of using the prodrug forms.

European Patent Application Publication No. 590789A1 and U.S. Pat. No. 5,446,051 disclose that certain decahydroisoquinoline derivatives are AMPA receptor antagonists, and as such are useful in the treatment of many different conditions, including pain. In addition, WO 98/45270, published Oct. 15, 1998, discloses that certain selective $GluR_5$ antagonists are useful for treating pain.

It is an object of the present invention to provide diesters of 3S,4aR,6S,8aR-6-(((4-carboxy)phenyl)methyl)-1,2,3,4,4a,5,6,7,8,8a-decahydroisoquinoline-3-carboxylic acid which provide substantially improved bioavailability of the parent diacid in a patient. In addition, it is an object of the present invention to provide diesters of 3S,4aR,6S, 8aR-6-(((4-carboxy)phenyl)methyl)-1,2,3,4,4a,5,6,7,8,8a-decahydroisoquinoline-3-carboxylic acid which are substantially converted to the parent diacid in the patient.

It has now been found that novel diesters of the diacid, 3S,4aR,6S,8aR-6-(((4-carboxy)phenyl)methyl)-1,2,3,4,4a,5,6,7,8,8a-decahydroisoquinoline-3-carboxylic acid, possess substantially improved bioavailability as compared to the diacid. In addition, the diesters are substantially converted to the diacid in the patient. The diacid is generically disclosed in U.S. Pat. No. 5,446,051, issued Aug. 29, 1995, and specifically disclosed in, WO 98/45270, published Oct. 15, 1998, as a selective $GluR_5$ antagonist for treatment of pain.

Thus, the present invention provides compounds of formula I:

formula I

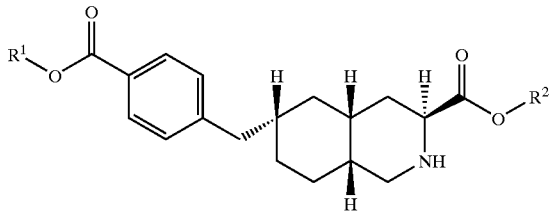

wherein $R^1$ and $R^2$ are each independently $C_1-C_{20}$ alkyl, $C_2-C_6$ alkenyl, $C_1-C_6$ alkylaryl, $C_1-C_6$ alkyl($C_3-C_{10}$) cycloalkyl, $C_1-C_6$ alkyl-N, N—$C_1-C_6$ dialkylamine, $C_1-C_6$ alkyl-pyrrolidine, $C_1-C_6$ alkyl-piperidine, or $C_1-C_6$ alkyl-morpholine; or a pharmaceutically acceptable salt thereof.

The present invention further provides a method of antagonizing the $GluR_5$ receptor, which comprises administering to a patient an effective amount of a compound of formula I.

In addition, the present invention provides a method for the treatment of pain, which comprises administering to a patient an effective amount of a compound of formula I.

The present invention further provides a method for the treatment of migraine, which comprises administering to a patient an effective amount of a compound of formula I.

The present invention further provides the use of a compound of formula I for the manufacture of a medicament for the treatment of pain.

The present invention further provides the use of a compound of formula I for the manufacture of a medicament for the treatment of migraine.

As used herein, the term "prodrug" refers to a diester derivative of a dicarboxylic acid functional drug, which derivative, when administered to a patient is converted into the diacid (drug). The enzymatic and/or chemical hydrolytic cleavage of the compounds of the present invention occurs in such a manner that the parent dicarboxylic acid (drug ) is released.

As used herein the term "Compound A" refers to 3S,4aR, 6S,8aR-6-(((4-carboxy)phenyl)methyl)-1,2,3,4,4a,5,6,7,8,8a-decahydroisoquinoline-3-carboxylic acid.

As used herein the term "Compound B" refers to 3S,4aR, 6S, 8aR-6-(((4-carboxy)phenyl)methyl)-1,2,3,4,4a,5,6,7,8,8a-decahydroisoquinoline-3-carboxylic acid HCl, diethyl ester.

As used herein the term "Compound C" refers to 3S,4aR, 6S, 8aR-6-(((4-carboxy)phenyl)methyl)-1,2,3,4,4a,5,6,7,8,8a-decahydroisoquinoline-3-carboxylic acid HCl, dimethyl ester.

As used herein the term "Compound D" refers to 3S,4aR, 6S, 8aR-6-(((4-carboxy)phenyl)methyl)-1,2,3,4,4a,5,6,7,8,8a-decahydroisoquinoline-3-carboxylic acid HCl, diisopropyl ester.

As used herein the term "Compound E" refers to 3S,4aR, 6S, 8aR-6-(((4-carboxy)phenyl)methyl)-1,2,3,4,4a,5,6,7,8,8a-decahydroisoquinoline-3-carboxylic acid HCl, diisobutyl ester.

As used herein the term "$C_1-C_4$ alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "$C_1-C_6$ alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like.

As used herein the term "$C_1-C_{10}$ alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like.

As used herein the term "$C_1-C_{20}$ alkyl" refers to a straight or branched, monovalent, saturated aliphatic chain of 1 to 20 carbon atoms and includes, but is not limited to, methyl, ethyl, propyl, isopropyl, butyl, isobutyl, t-butyl, pentyl, isopentyl, hexyl, 3-methylpentyl, 2-ethylbutyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-nonadecyl, n-eicosyl and the like.

As used herein, the terms "Me", "Et", "Pr", "iPr", "Bu" and "t-Bu" refer to methyl, ethyl, propyl, isopropyl, butyl and tert-butyl respectively.

As used herein the term "$C_2-C_6$ alkenyl" refers to a straight or branched, monovalent, unsaturated aliphatic chain having from two to six carbon atoms. Typical $C_2-C_6$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

As used herein, the term "aryl" refers to monovalent carbocyclic group containing one or more fused or nonfused phenyl rings and includes, for example, phenyl, 1- or 2-naphthyl, 1,2-dihydronaphthyl, 1,2,3,4-tetrahydronaphthyl, and the like.

As used herein, the term "$C_1$–$C_6$ alkylaryl" refers to a straight or branched, monovalent, saturated aliphatic chain of 1 to 6 carbon atoms which has an aryl group attached to the aliphatic chain. Included within the term "$C_1$–$C_6$ alkylaryl" are the following:

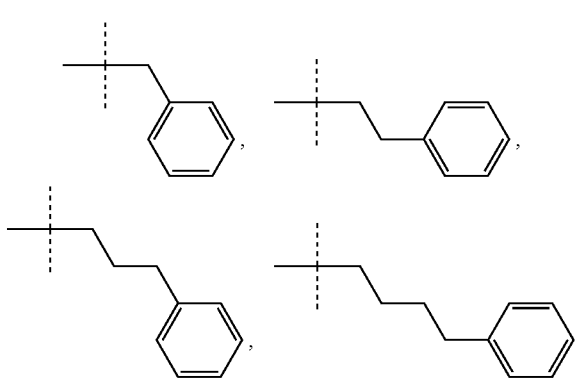

and the like.

As used herein the term "($C_3$–$C_{10}$)cycloalkyl" refers to a saturated hydrocarbon ring structure containing from three to ten carbon atoms. Typical $C_3$–$C_{10}$ cycloalkyl groups include cyclopropyl, cyclobutyl, cyclopentyl, cyclohexyl, cycloheptyl, cyclooctyl, and the like. It is understood that "($C_3$–$C_8$)cycloalkyl" and "($C_4$–$C_6$)cycloalkyl" is included within the term "($C_3$–$C_{10}$)cycloalkyl".

As used herein, the term "$C_1$–$C_6$ alkyl($C_3$–$C_{10}$)cycloalkyl" refers to a straight or branched, monovalent, saturated aliphatic chain of 1 to 6 carbon atoms which has a ($C_3$–$C_{10}$)cycloalkyl attached to the aliphatic chain. Included within the term "$C_1$–$C_6$ alkyl($C_3$–$C_{10}$)cycloalkyl" are the following:

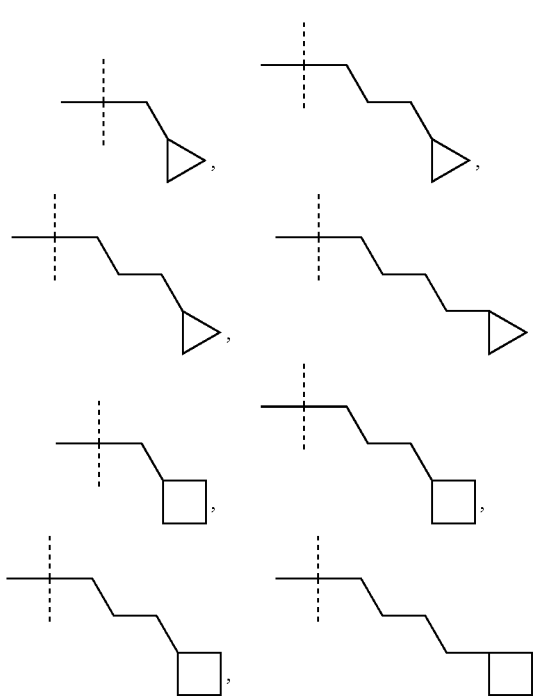

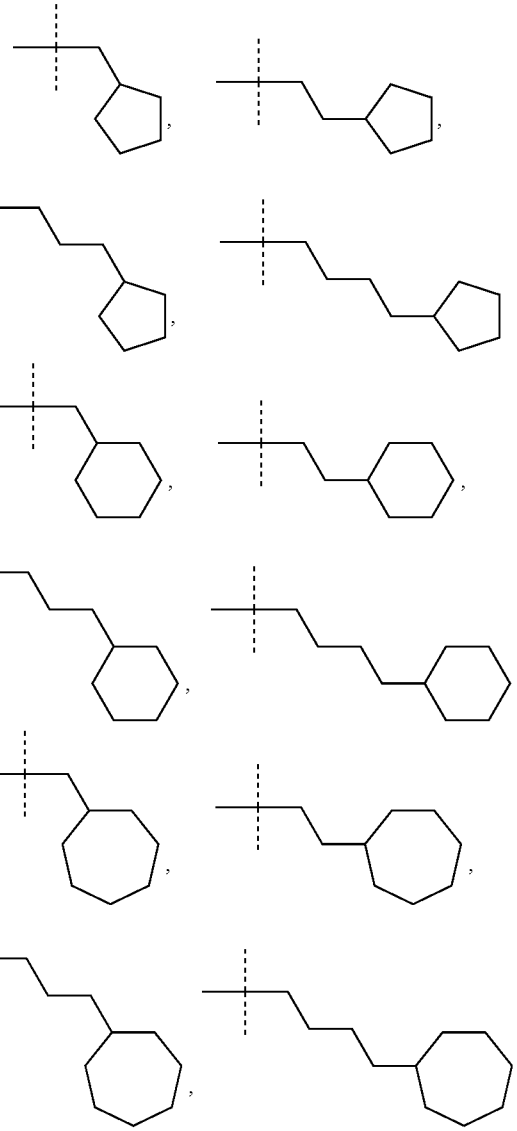

and the like

As used herein the term "N,N—$C_1$–$C_6$ dialkylamine" refers to a nitrogen atom substituted with two straight or branched, monovalent, saturated aliphatic chains of 1 to 6 carbon atoms. Included within the term "N,N—$C_1$–$C_6$ dialkylamine" are —N($CH_3$)$_2$, —N($CH_2CH_3$)$_2$, —N($CH_2CH_2CH_3$)$_2$, —N($CH_2CH_2CH_2CH_3$)$_2$, and the like.

As used herein the term "$C_1$–$C_6$ alkyl-N,N—$C_1$–$C_6$ dialkylamine" refers to straight or branched, monovalent, saturated aliphatic chain of 1 to 6 carbon atoms which has an N,N—$C_1$–$C_6$ dialkylamine attached to the aliphatic chain. Included within the term "$C_1$–$C_6$ alkyl-N,N—$C_1$–$C_6$ dialkylamine" are the following:

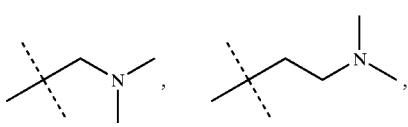

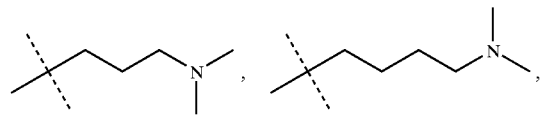
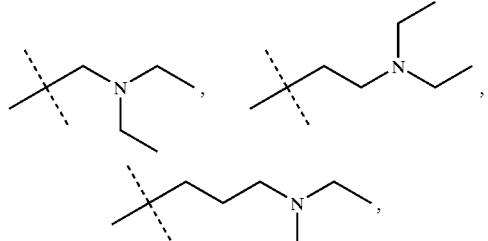
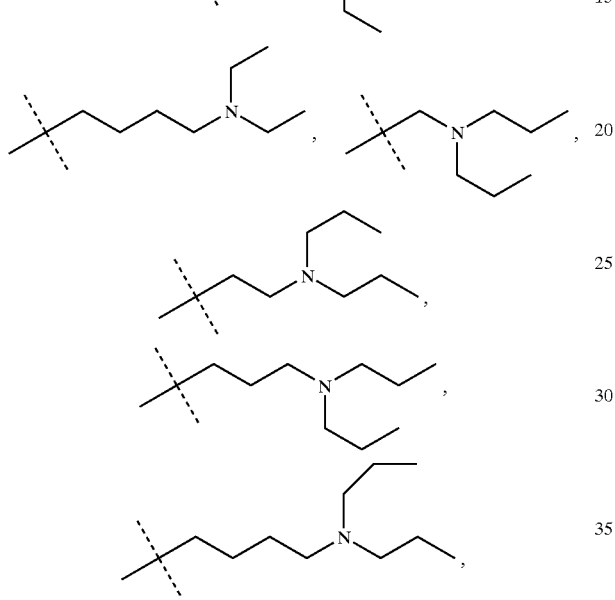

and the like.

As used herein the term "$C_1$–$C_6$ alkyl-pyrrolidine" refers to a straight or branched, monovalent, saturated aliphatic chain of 1 to 6 carbon atoms which has a pyrrolidine attached to the aliphatic chain. Included within the scope of the term "$C_1$–$C_6$ alkyl-pyrrolidine" are the following:

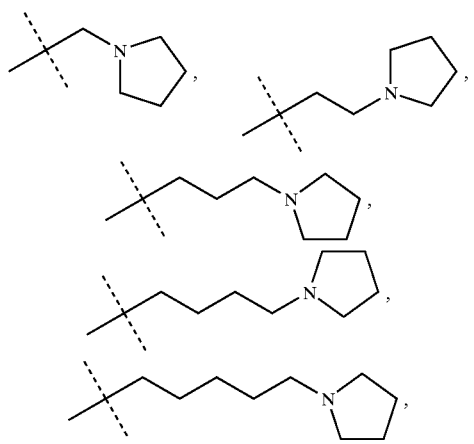

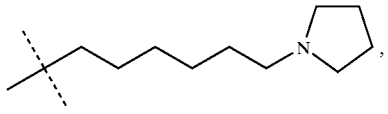

and the like.

As used herein the term "$C_1$–$C_6$ alkyl-piperidine" refers to a straight or branched, monovalent, saturated aliphatic chain of 1 to 6 carbon atoms which has a piperidine attached to the aliphatic chain. Included within the scope of the term "$C_1$–$C_6$ alkyl-piperidine" are the following:

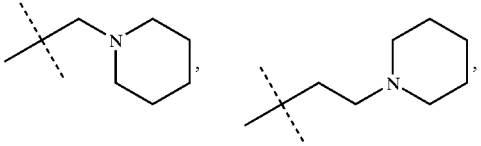
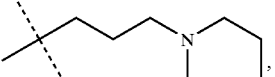
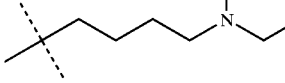
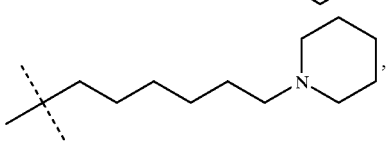

and the like.

As used herein the term "$C_1$–$C_6$ alkyl-morpholine" refers to a straight or branched, monovalent, saturated aliphatic chain of 1 to 6 carbon atoms which has a morpholine attached to the aliphatic chain. Included within the scope of the term "$C_1$–$C_6$ alkyl-morpholine" are the following:

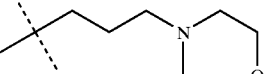
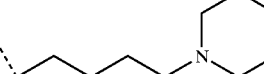
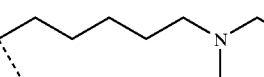
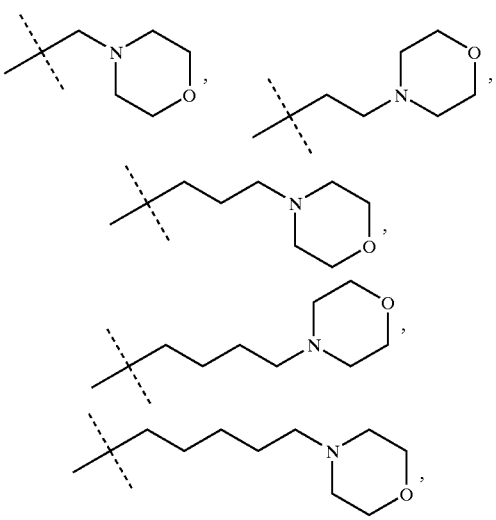

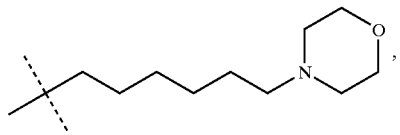

and the like.

The designation

———▶ refers to a bond that protrudes forward out of the plane of the page.

The designation

·······|||| refers to a bond that protrudes backward out of the plane of the page.

This invention includes the hydrates and the pharmaceutically acceptable salts of the compounds of formula I. A compound of this invention can possess a sufficiently basic functional group which can react with any of a number of inorganic and organic acids, to form a pharmaceutically acceptable salt.

The term "pharmaceutically acceptable salt" as used herein, refers to salts of the compounds of formula I which are substantially non-toxic to living organisms. Typical pharmaceutically acceptable salts include those salts prepared by reaction of the compounds of the present invention with a pharmaceutically acceptable mineral or organic acid. Such salts are also known as acid addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid, oxalic acid and methanesulfonic acid.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that such salts may exist as a hydrate.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formula I can be resolved by one of ordinary skill in the art using standard techniques well known in the art, such as those described by J. Jacques, et al., "Enantiomers, Racemates, and Resolutions", John Wiley and Sons, Inc., 1981.

The compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

The specific stereoisomers and enantiomers of compounds of formula (I) can be prepared by one of ordinary skill in the art utilizing well known techniques and processes, such as those disclosed by Eliel and Wilen, "Stereochemistry of Organic Compounds", John Wiley & Sons, Inc., 1994, Chapter 7, Separation of Stereoisomers. Resolution. Racemization, and by Collet and Wilen, "Enantiomers, Racemates, and Resolutions", John Wiley & Sons, Inc., 1981. For example, the specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

The compounds of formula I can be prepared by techniques and procedures readily available to one of ordinary skill in the art. For example, various starting materials and general procedures which may be employed by one of ordinary skill in the art in the preparation of compounds of formula I are described in U.S. Pat. No. 5,446,051, issued Aug. 29, 1995, which is hereby incorporated by reference, and WO 98/45270, published Oct. 15, 1998.

More specifically, compounds of formula I can be prepared by following the procedures as set forth in Scheme I. This scheme is not intended to limit the scope of the invention in any way. All substituents, unless otherwise indicated, are previously defined. The reagents and starting materials are readily available to one of ordinary skill in the art.

Scheme I

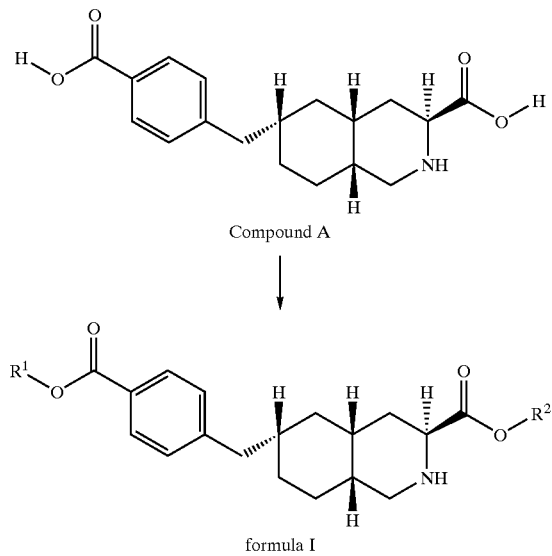

Compound A

↓ formula I

In Scheme I, compound A is esterified to provide the diester of formula I under standard conditions well known in the art. For example, compound A is dissolved in a suitable organic solvent and treated with a suitable acid, such as hydrochloric acid. Examples of suitable organic solvents include, methyl alcohol, ethyl alcohol, propyl alcohol, isopropyl alcohol, n-butyl alcohol, isobutyl alcohol, t-butyl alcohol, pentyl alcohol, isopentyl alcohol, hexyl alcohol, 3-methylpentyl alcohol, 2-ethylbutyl alcohol, n-heptyl alcohol, n-octyl alcohol, and the like. The reaction is heated at about 40° C. to about 60° C. for about 4 hours to about 16 hours. The product is then isolated and purified using techniques well known to one of ordinary skill in the art, such as extraction techniques and chromatography.

For example, the above reaction is cooled, diluted with a suitable organic solvent, such as ethyl acetate, washed with saturated sodium bicarbonate, brine, dried over anhydrous magnesium sulfate, filtered and concentrated under vacuum to provide the compound of formula I. This material may be further purified by flash chromatography on silica gel with a suitable eluent such as ethyl acetate/hexane.

Alternatively, compound A is dissolved in a suitable organic solvent and treated with an excess of thionyl chloride. Examples of suitable organic solvents are anhydrous methyl alcohol, ethyl alcohol, propyl alcohol, isopropyl alcohol, butyl alcohol, isobutyl alcohol, t-butyl alcohol, pentyl alcohol, isopentyl alcohol, hexyl alcohol, 3-methylpentyl alcohol, 2-ethylbutyl alcohol, n-heptyl alcohol, n-octyl alcohol, and the like. The solution is stirred at reflux for about 1 to 3 hours, and at room temperature for about 8 to 16 hr. The mixture is then concentrated under vacuum, and the residue is purified in a manner analogous to the procedures described above to provide the prodrug diester of formula I.

The pharmaceutically acceptable salts of formula I are readily prepared by one of ordinary skill in the art using standard techniques and procedures. For example, the above product is suspended in diethyl ether, which has been saturated with HCl gas. The mixture is stirred for about 1 to 3 hours. The precipitate is then filtered and washed with diethyl ether under vacuum to provide the pharmaceutically acceptable salt of the prodrug diester of formula I.

The following examples illustrate the invention and represent typical syntheses of the compounds of formula I as described generally above. The reagents and starting materials are readily available to one of ordinary skill in the art. As used herein, the following terms have the meanings indicated: "eq" or "equiv." refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "min" refers to minutes; "h" refers to hours; "° C." refers to degrees Celsius; "TLC" refers to thin layer chromatography; "HPLC" refers to high performance liquid chromatography; "δ" refers to part per million down-field from tetramethylsilane; "THF" refers to tetrahydrofuran; "DMF" refers to N,N-dimethylformamide; "DMSO" refers to methyl sulfoxide; "aq" refers to aqueous; "EtOAc" refers to ethyl acetate; "iPrOAc" refers to isopropyl acetate; "MeOH" refers to methanol; "MTBE" refers to tert-butyl methyl ether, and "RT" refers to room temperature.

PREPARATION 1

Preparation of 3S,4aR,6S,8aR-6-(((4-carboxy)phenyl)methyl)-1,2,3,4,4a,5,6,7,8,8a-decahydroisoquinoline-3-carboxylic acid (Compound A).

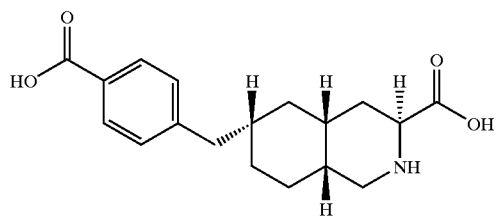

A. Methyl 4-(diethylphosphonomethyl)benzoate: A solution of 25.0 g (110 mmol) of methyl 4-bromomethylbenzoate and 37 mL (36.3 g, 220 mmol) of triethyl phosphite in 150 mL of toluene was heated for 18 hours at reflux, then cooled and concentrated in vacuo. Chromatography (400 g of silica gel, ethyl acetate) of the residue afforded 30.6 g (98%) of the title compound.

B. Ethyl 3S,4aR,6S,8aR-6-(((4-methoxycarbonyl)phenyl)-methyl)-1,2,3,4,4a,5,6,7,8,8a-decahydroisoquinoline-3-carboxylate: 14.1 g (49.4 mmol) of the compound from step A above, and 48 mL (of a 1.0 M solution) of sodium bis(trimethyl-silyl)amide in 100 mL of THF was stirred 45 min at 0° C., then treated with 10.0 g of ethyl 3S,4aR,8aR-6-oxo-2-methoxy-carbonyl-1,2,3,4,4a,5,6,7,8,8a-decahydroisoquinoline-3-carboxylate in 40 mL of THF. After 15 minutes at 0° C., the reaction was quenched with 100 mL of water and extracted three times with 150 mL each of ether. The combined organics were dried (magnesium sulfate), filtered and concentrated in vacuo. The residue was dissolved in 500 mL of ether, treated with 3.0 g of 5% palladium on carbon, and hydrogenated at room temperature and one atmosphere of hydrogen for 24 hours. The mixture was diluted with 500 mL of ether, filtered through a pad of diatomaceous earth, and the filtrate concentrated in vacuo. Chromatography (400 g of silica gel, 25% ethyl acetate/hexane) of the residue afforded 12.0 g (81%) of the title compound, as a mixture of methyl and ethyl esters from transesterification of the methyl ester during hydrogenation.

C. 12.0 g of the compound from step B above, was heated to reflux for 18 hours with 100 mL of 6N hydrochloric acid, then cooled to room temperature. The resulting solid was filtered, washing with water, acetone and ether, and dried in vacuo at 60° C. to afford 6.2 g (57%) of the title compound.

Analysis calculated for $C_{18}H_{23}NO_4 \cdot HCl \cdot 1.25\ H_2O$: C, 57.44; H, 7.10; N, 3.72. Found: C; 57.44; H, 6.69; N, 3.76. $[a]_D=-4.8°$ (c=1, 1N HCl).

EXAMPLE 1

Preparation of 3S4aR,6S,8aR-6-(((4-carboxy)phenyl)methyl)-1,2,3,4,4a,5,6,7,8,8a-decahydroisoguinoline-3-carboxylic acid HCl, Dimethyl Ester (Compound C).

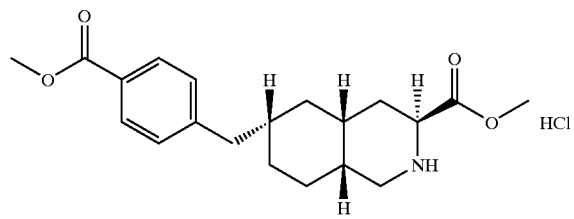

To a solution of 0.7 g (2.0 mmol) of 3S,4aR,6S, 8aR-6-(((4-carboxy)phenyl)methyl)-1,2,3,4,4a,5,6,7,8,8a-decahydroisoquinoline-3-carboxylic acid (See preparation 1) in 80 mL of anhydrous methyl alcohol was added 3.0 mL (41.1 mmol) of thionyl chloride. The solution was stirred at refluxing temperature for 2.5 hr and at room temperature for 14 hr. The mixture was concentrated in vacuo and the residue was suspended in ether and filtered. The white solid was washed three times with ether and dried to afford 0.65 g (85%) of the title compound.

Analysis calculated for $C_{20}H_{27}ClNO_4$: %C, 62.90; %H, 7.39; %N, 3.67. Found: %C, 63.11; %H, 7.65; %N, 3.68. Ionspray Mass Spectrum: $[M+H-HCl]^+=346$.

EXAMPLE 2

Preparation of 3S,4aR,6S,8aR-6-(((4-carboxy)phenyl)methyl)-1,2,3,4,4a,5,6,7,8,8a-decahydroisoguinoline-3-carboxylic acid HCl, Diethyl Ester, (Compound B).

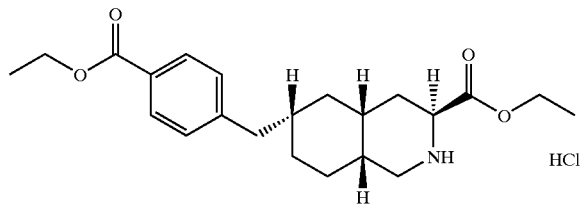

A solution of 2.0 g (5.6 mmol) of 3S,4aR,6S, 8aR-6-(((4-carboxy)phenyl)methyl)-1,2,3,4,4a,5,6,7,8,8a-decahydroisoquinoline-3-carboxylic acid (See preparation 1) in 10 mL punctilious ethyl alcohol saturated with hydrochloric acid (g) was heated at refluxing temperature for 18 hr. The mixture was cooled and concentrated in vacuo and the residue was suspended in ether and filtered. The white solid was washed three times with ether and dried to afford 2.1 g (91%) of the title compound.

Analysis calculated for $C_{22}H_{32}ClNO_4 \cdot 0.25H_2O$: %C, 63.76; %H, 7.90; %N, 3.38. Found: %C, 63.53; %H, 7.74; %N, 4.25. Ionspray Mass Spectrum: $[M+H-HCl]^+=374$.

EXAMPLE 3

Preparation of 3S,4aR,6S,8aR-6-(((4-carboxylphenyl)methyl)-1,2,3,4,4a,5,6,7,8,8a-decahydroisoguinoline-3-carboxylic acid HCl, diisopropyl ester, (Compound D).

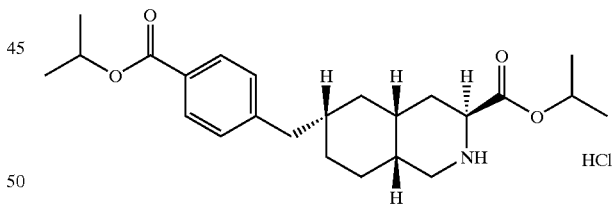

To a solution of 0.7 g (2.0 mmol) of 3S,4aR,6S, 8aR-6-(((4-carboxy)phenyl)methyl)-1,2,3,4,4a,5,6,7,8,8a-decahydroisoquinoline-3-carboxylic acid (See preparation 1) in 80 mL of anhydrous isopropyl alcohol was added 3.0 mL (41.1 mmol) of thionyl chloride. The solution was stirred at refluxing temperature for 2.5 hr and at room temperature for 14 hr. The mixture was concentrated in vacuo and the residue was suspended in ether and filtered. The white solid was washed three times with ether and dried to afford 0.60 g (68%) of the title compound.

Analysis calculated for $C_{24}H_{35}ClNO_4 \cdot 0.3H_2O$: %C, 65.01; %H, 8.09; %N, 3.16. Found: %C, 64.82; %H, 8.34; %N, 3.32. Ionspray Mass Spectrum: $[M+H-HCl]^+=402$.

EXAMPLE 4

Preparation of 3S,4aR,6S,8aR-6-(((4-carboxy) phenyl)methyl)-1,2,3,4,4a,5,6,7,8,8a-decahydroisoquinoline-3-carboxylic acid HCl, Diisobutyl Ester (Compound E).

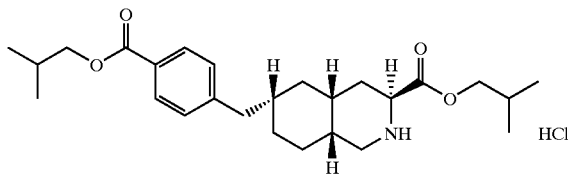

To a solution of 0.7 g (2.0 mmol) of 3S,4aR, 6S,8aR-6-(((4-carboxy)phenyl)methyl)-1,2,3,4,4a,5,6,7,8,8a-decahydroisoquinoline-3-carboxylic acid (See preparation 1) in 80 mL of anhydrous 2-methyl-1-propanol was added 3.0 mL (41.1 mmol) of thionyl chloride. The solution was stirred at 110° C. for 3.5 hr and at room temperature for 14 hr. The mixture was concentrated in vacuo and the residue was partitioned between 30 mL of ethyl acetate and 50 mL sat. sodium bicarbonate. The organic layer was separated and the aqueous layer was extracted one time with 30 mL of ethyl acetate. The combined organic extracts were dried ($Na_2SO_4$), filtered and concentrated in vacuo.

Chromatography (50 g of silica gel, 3% methyl alcohol/ dichloromethane) of the residue afforded 0.7 g of material. The material was dissolved in 6 mL ether and 15 mL 1N hydrochloric acid (g) in ether. The white solid was filtered and washed three times with ether and dried to afford 0.66 g (71%) of the title compound.

Analysis calculated for $C_{26}H_{39}ClNO_4 \cdot 0.7H_2O$: %C, 65.24; %H, 8.72; %N, 2.93. Found: %C, 65.08; %H, 8.40; %N, 3.03. Ionspray Mass Spectrum: $[M+H-HCl]^+=430$.

Pharmacological Results

The following in vivo data, in rats, dogs and monkeys, exemplify the surprising improvement in bioavailability of the diester prodrugs of the present invention over the diacid of 3S,4aR,6S, 8aR-6-(((4-carboxy)phenyl)methyl)1,2,3,4,4a,5,6,7,8,8a-decahydroisoquinoline-3-carboxylic acid. Percent bioavailability is determined using the following equation:

$$\frac{\text{AUC p.o.}}{\text{AUC i.v.}} \times \frac{\text{dose i.v.}}{\text{dose p.o.}} \times 100 = \% \text{ Bioavailability}$$

wherein AUC represents the area under the curve, p.o. represents oral dose, and i.v. represents intravenous dose.

Bioavailability in Dogs:

Beagle dogs (2 male and 1 female) were administered an oral and iv dose of 3S,4aR,6S,8aR-6-(((4-carboxy)phenyl) methyl)-1,2,3,4,4a,5,6,7,8,8a-decahydroisoquinoline-3-carboxylic acid (10 mg/kg) to determine oral bioavailability. The same three dogs were also administered an oral 10 mg/kg dose of compound 3S,4aR,6S,8aR-6-(((4-carboxy) phenyl)methyl)-1,2,3,4,4a,5,6,7,8,8a-decahydroisoquinoline-3-carboxylic acid, diethyl ester, to determine whether the prodrug would increase bioavailability. The plasma concentrations of 3S,4aR,6S,8aR-6-(((4-carboxy)phenyl)methyl)-1,2,3,4,4a,5,6,7,8,8a-decahydroisoquinoline-3-carboxylic acid were determined by LC/MS/MS.

Study Methods:

Live Phase: 3S,4aR,6S,8aR-6-(((4-carboxy)phenyl) methyl)-1,2,3,4,4a,5,6,7,8,8a-decahydroisoquinoline-3-carboxylic acid (HCl salt) was dissolved in dilute sodium hydroxide for oral administration (15 mg/ml) and in ethano/ dilute sodium hydroxide for iv administration (30 mg/ml). 3S,4aR,6S,8aR-6-(((4-carboxy)phenyl)methyl)-1,2,3,4,4a, 5,6,7,8,8a-decahydroisoquinoline-3-carboxylic acid, diethyl ester (HCl salt) was dissolved in water for oral administration (15 mg/ml). Dogs weighed between 12 to 15 kg.

Results:

The oral bioavailability for 3S,4aR,6S, 8aR-6-(((4-carboxy)phenyl)methyl)-1,2,3,4,4a,5,6,7,8,8a-decahydroisoquinoline-3-carboxylic acid was determined to be 5.6% in dogs. When 3S,4aR,6S, 8aR-6-(((4-carboxy) phenyl)methyl)-1,2,3,4,4a,5,6,7,8,8a-decahydroisoquinoline-3-carboxylic acid HCl, diethyl ester was administered, bioavailability increased to 50.3%. The use of 3S,4aR,6S,8aR-6-(((4-carboxy)phenyl)methyl)-1,2,3, 4,4a,5,6,7,8,8a-decahydroisoquinoline-3-carboxylic acid HCl, diethyl ester, provided approximately a 9 fold increase in bioavailability over 3S, 4aR,6S,8aR-6-(((4-carboxy) phenyl)methyl)-1,2,3,4,4a,5,6,7,8,8a-decahydroisoquinoline-3-carboxylic acid.

Tables 1 and 2 below summarize the pharmacokinetic parameters found for Compounds A and B following 10 mg/kg administration (i.v. or p.o.) to Beagle Dogs and Fischer Rats respectively.

TABLE 1

Pharmacokinetic Parameters of Compound A in Beagle Dogs after a 10 mg/kg dose of Compound A or the Diester Prodrug, Compound B.

| Compound | $T_{max}$ (hr) | $C_{max}$ (ng/mL) | AUC (ng hr/mL) | % Bioavail | Improvement |
|---|---|---|---|---|---|
| A (diacid), i.v. (10 mg/kg) | — | 28,791 | 41,432 | — | |
| A (diacid), p.o. (10 mg/kg) | 2 | 473 | 2,320 | 5.6 | 1 |
| B (diester), p.o. (10 mg/kg) | 1 | 3,829 | 20,827 | 50.3 | 9X |

TABLE 2

Pharmacokinetic Parameters of Compound A in Fischer Rats after a 10 mg/kg Dose of Compound A or the Diester Prodrug, Compound B.*

| Compound | $T_{max}$ (hr) | $C_{max}$ (ng/mL) | AUC (ng hr/mL) | % Bioavail | Improvement |
|---|---|---|---|---|---|
| A (diacid), i.v. (10 mg/kg) | — | 6,281 | 2,410 | — | |
| A (diacid), p.o. (10 mg/kg) | 0.5 | 24 | 39 | 1.6 | 1 |
| B (diester), p.o. (10 mg/kg) | 1 | 539 | 1,506 | 62.5 | 39X |

*The above pharmacokinetic parameters were obtained under standard conditions in a manner analogous to the procedures used for obtaining similar data for Beagle dogs in Table 1.

Table 3 below summarize the pharmacokinetic parameters found for Compounds B, C, D and E following 30 mg-equiv./kg Oral Administration to Fischer Rats.

TABLE 3

Pharmacokinetic Parameters of Compound A in Fischer Rats after a 30 mg equiv./kg Oral Dose of Diester Prodrug Compounds B, C, D, and E

| Compound | $T_{max}$ (hr) | $C_{max}$ (ng/mL) | AUC (ng hr/mL) | % Bioavail |
|---|---|---|---|---|
| B diethyl ester | 0.5 | 2,295 | 3,600 | 65.6 |
| C dimethyl ester | 0.5 | 1,958 | 4,352 | 79.3 |
| D diisopropyl ester | 0.5 | 2,392 | 3,901 | 71.1 |
| E diisobutyl ester | 0.5 | 1,503 | 4,383 | 79.9 |

Bioavailability in Cynomolgus Monkeys

Four female monkeys were administered an oral and iv dose of compound A (oral: 10 mg/kg; iv: 1 mg/kg) to determine oral bioavailability. The same animals were also administered an oral 10 mg/kg dose of compound B. The plasma concentrations of compound A were determined by LC/MS/MS.

Study Design

Four female cynomolgus monkeys were given a single iv dose of compound A (1 mg/kg) on day 0, a single oral dose of compound A (10 mg/kg) on day 6 and a single oral dose of compound B (10 mg/kg) on day 10. Blood was collected at 0.5, 1, 2, 3, 4, 5, 6 and 8 hours post dose for oral dosing and 0.167, 0.33, 0.67, 1, 1.5, 2, 3 and 4 hours post dose for iv dosing. Dosing solutions for compound A and compound B were prepared in water. Sodium hydroxide was added to the compound A iv dosing solution to completely dissolve compound A. Following a single iv dose of compound A to monkeys, compound A was eliminated from plasma rapidly with a terminal half-life of 0.7 hr and a plasma clearance of 14 ml/min/kg. After an oral dose of compound A, measurable levels of drug were detected at 0.5 hr and the $C_{max}$ (127 ng/ml) was obtained at 1 hour, indicating the drug was rapidly absorbed. Measurable levels of drug (>10 ng/ml) were still present 8 hours post dose. The absolute bioavailability of compound A was low (11.1%). The prodrug, compound B, was also rapidly absorbed, as the $C_{max}$ (1,346 ng/ml) was observed 1 hr post dose. No detectable plasma levels of compound B were observed at any time point. Bioavailability was estimated at 34.8%. The use of compound B resulted in a 3.1 fold increase in the bioavailability.

Table 4 below summarizes the pharmacokinetic parameters found for Compounds A and B following i.v. or oral administration to Cynomolgus Monkeys.

TABLE 4

Pharmacokinetic Parameters of Compound A in Cynomolgus Monkeys after an i.v. and p.o. Dose of Compound A or the Diester Prodrug, Compound B.

| Compound | $T_{max}$ (hr) | $C_{max}$ (ng/mL) | AUC (ng hr/mL) | % Bioavail | Improvement |
|---|---|---|---|---|---|
| A (diacid), i.v. (1 mg/kg) | — | 1,922 | 1,191 | — | |
| A (diacid), p.o. (10 mg/kg) | 1 | 127 | 1,320 | 11.1 | 1 |
| B (diester), p.o. (10 mg/kg) | 1 | 1,346 | 4,149 | 34.8 | 3.1X |

The present invention further provides a method of antagonizing the GluR$_5$ receptor, which comprises administering to a patient an effective amount of a compound of formula I. As such, the compounds of the present invention are useful for treating pain and migraine. The forms of pain which fall within the general term "pain" which may be treated according to the invention include severe pain, chronic pain, intractable pain, neuropathic pain, mild pain, persistent pain, and the like.

Thus, the present invention further provides a method for the treatment of pain, which comprises administering to a patient an effective amount of a compound of formula I.

As used herein the term "patient" refers to a mammal, such a mouse, guinea pig, rat, dog or human. It is understood that the preferred patient is a human.

The term "treating" (or "treat") as used herein includes its generally accepted meaning which encompasses prohibiting, preventing, restraining, and slowing, stopping, or reversing progression, severity, of a resultant symptom. As such, the methods of this invention encompass both therapeutic and prophylactic administration.

As used herein the term "effective amount" refers to the amount or dose of the compound, upon single or multiple dose administration to the patient, which provides the desired effect in the patient under diagnosis or treatment.

An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

In effecting treatment of a patient afflicted with a condition, disease or disorder described above, a compound of formula (I) can be administered in any form or mode which makes the compound bioavailable in effective amounts, including oral and parenteral routes. For example, compounds of formula (I) can be administered orally, subcutaneously, intramuscularly, intravenously, transdermally, intranasally, rectally, buccally, and the like. Alternatively, the compound may be administered by continuous infusion. Oral administration is generally preferred. One skilled in the art of preparing formulations can readily select the proper form and mode of administration depending upon the particular characteristics of the compound selected, the disease state to be treated, the stage of the disease, and other relevant circumstances.

It will be understood by the skilled reader that all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

According to another aspect, the present invention provides a pharmaceutical composition, which comprises a compound of formula I or a pharmaceutically acceptable salt thereof as defined hereinabove and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1

Hard gelatin capsules are prepared using the following ingredients:

|  | Quantify (mg/capsule) |
| --- | --- |
| Prodrug | 250 |
| Starch, dried | 200 |
| Magnesium Stearate | 10 |
| Total | 460 |

The above ingredients are mixed and filled into hard gelatin capsules in 460 mg quantities.

Formulation 2

Tablets each containing 60 mg of active ingredient are made as follows:

|  | Quantity (mg/tablet) |
| --- | --- |
| Prodrug | 60 |
| Starch | 45 |
| Microcrystalline Cellulose | 35 |
| Polyvinylpyrrolidone | 4 |
| Sodium Carboxymethyl Starch | 4.5 |
| Magnesium Stearate | 0.5 |
| Talc | 1 |
| Total | 150 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

What is claimed is:

1. A compound of the formula:

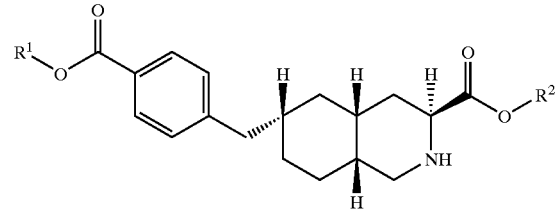

wherein $R^1$ and $R^2$ are each independently $C_1$–$C_{20}$ alkyl, $C_2$–$C_6$ alkenyl, $C_1$–$C_6$ alkylaryl, $C_1$–$C_6$ alkyl($C_3$–$C_{10}$) cycloalkyl, $C_1$–$C_6$ alkyl-N,N—$C_1$–$C_6$ dialkylamine, $C_1$–$C_6$ alkyl-pyrrolidine, $C_1$–$C_6$ alkyl-piperidine, or $C_1$–$C_6$ alkyl-morpholine; or a pharmaceutically acceptable salt thereof.

2. A compound according to claim 1 wherein $R^1$ and $R^2$ are each independently $C_1$–$C_{10}$ alkyl.

3. A compound according to claim 2 wherein $R^1$ and $R^2$ are each independently $C_1$–$C_4$ alkyl.

4. A compound according to claim 3 wherein $R^1$ and $R^2$ are each independently methyl, ethyl, propyl, isopropyl, butyl, or isobutyl.

5. A compound according to claim 4 wherein $R^1$ and $R^2$ are each methyl.

6. A compound according to claim 4 wherein $R^1$ and $R^2$ are each isopropyl.

7. A compound according to claim 4 wherein $R^1$ and $R^2$ are each isobutyl.

8. A compound which is 3S,4aR,6S, 8aR-6-(((4-carboxy) phenyl)methyl)-1,2,3,4,4a,5,6,7,8,8a-decahydroisoquinoline-3-carboxylic acid, diethyl ester or a pharmaceutically acceptable salt thereof.

9. A compound according to claim 8 wherein the pharmaceutically acceptable salt is a hydrochloride salt.

10. A compound which is 3S,4aR,6S,8aR-6-(((4-carboxy) phenyl)methyl)-1,2,3,4,4a,5,6,7,8,8a-decahydroisoquinoline-3-carboxylic acid, diethyl ester.

11. A pharmaceutical composition, which comprises a compound as claimed in claim 1 and a pharmaceutically acceptable diluent or carrier.

12. A method of treating pain, which comprises administering to a patient an effective amount of a compound of the formula:

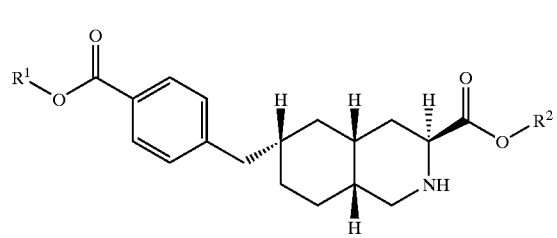

wherein $R^1$ and $R^2$ are each independently $C_1$–$C_{20}$ alkyl, $C_2$–$C_6$ alkenyl, $C_1$–$C_6$ alkylaryl, $C_1$–$C_8$ alkyl($C_3$–$C_{10}$) cycloalkyl, $C_1$–$C_6$ alkyl-N,N—$C_1$–$C_6$ dialkylamine, $C_1$–$C_6$ alkyl-pyrrolidine, $C_1$–$C_6$ alkyl-piperidine, or $C_1$–$C_6$ alkyl-morpholine; or a pharmaceutically acceptable salt thereof.

13. A method of treating migraine, which comprises administering to a patient an effective amount of a compound of the formula:

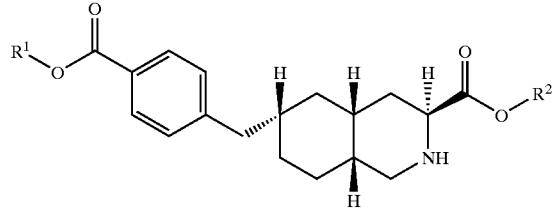

wherein $R^1$ and $R^2$ are each independently $C_1$–$C_{20}$ alkyl, $C_2$–$C_6$ alkenyl, $C_1$–$C_6$ alkylaryl, $C_1$–$C_6$ alkyl($C_3$–$C_{10}$) cycloalkyl, $C_1$–$C_6$ alkyl-N,N—$C_1$–$C_6$ dialkylamine, $C_1$–$C_6$ alkyl-pyrrolidine, $C_1$–$C_6$ alkyl-piperidine, or $C_1$–$C_6$ alkyl-morpholine; or a pharmaceutically acceptable salt thereof.

* * * * *